United States Patent [19]

Grote et al.

[11] Patent Number: 4,661,296

[45] Date of Patent: Apr. 28, 1987

[54] HF SEPARATION IN A CARBONYLATION PROCESS

[75] Inventors: Dace Grote, Columbus, Ohio; Bhupendra C. Trivedi, Godhra, India; Thomas O. Mason, Columbus, Ohio

[73] Assignee: Ashland Oil, Inc., Ashland, Ky.

[21] Appl. No.: 416,815

[22] Filed: Sep. 13, 1982

[51] Int. Cl.$^4$ .................. C07C 51/14; C07C 51/47
[52] U.S. Cl. ..................................... 260/413; 260/419; 562/400; 562/497; 562/521; 562/606
[58] Field of Search .............. 562/521, 497, 606, 400; 260/413, 419

[56] References Cited

U.S. PATENT DOCUMENTS 4,270,983  6/1981  Trivedi et al. ................. 562/521

FOREIGN PATENT DOCUMENTS 46-35722  10/1971  Japan ................................. 562/521
51-56409   5/1976  Japan ................................. 562/521
1174209   12/1969  United Kingdom ............... 562/521

Primary Examiner—Vivian Garner
Attorney, Agent, or Firm—John F. Jones

[57] ABSTRACT

In the preparation of a carboxylic acid by the carbonylation of an olefin in the presence of hydrofluoric acid catalyst, the hydrofluoric acid is isolated from the carboxylic acid by means of an ion-permeable membrane and the thus-isolated hydrofluoric acid can be recycled to again catalyze the carbonylation reaction.

4 Claims, No Drawings

HF SEPARATION IN A CARBONYLATION PROCESS

This invention relates to an improvement in the production of mono-carboxylic acids by carbonylation of olefins in the presence of an acid catalyst and water, commonly known as the Koch Reaction.

The production of fatty acids by high pressure synthesis from olefins, carbon monoxide and water in the presence of a variety of catalysts has been known for some time. Articles have been written and numerous patents have been granted for various embodiments of this process.

In the so-called Koch carbonylation reaction which is more fully prescribed in U.S. Pat. No. 2,831,877, the synthesis of carboxylic acids can be carried out under relatively mild conditions in the liquid phase with or without water followed by the addition of water. As an example, propylene is converted to isobutyric acid by reaction with carbon monoxide and hydrofluoric acid and water as follows:

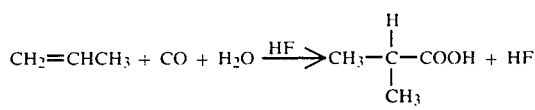

Thus, one mole of carbon monoxide and one mole of water are required to convert one mole of propylene to isobutyric acid and HF is the catalyst.

The Koch reaction has wide application. Thus, aliphatic olefins such as ethylene, propene, butene, isobutene, or higher molecular weight olefins such as nonene, hexadecene, and the like, and mixtures thereof, as, for example, the olefin-rich products of the Fischer-Tropsch synthesis carried out uner moderate pressure in the presence of catalysts, can be applied to cyclic olefins, such as cyclohexene, and the like can be used as starting materials in the reaction.

In the Koch process it is preferred that the reaction be carried out in such a manner that the olefins first contact the catalyst in the presence of carbon monoxide. Preferably the olefins are only introduced when the catalyst and the catalyst space have been saturated with carbon monoxide. If olefins are first introduced into the catalyst, for example, into hydrofluoric acid, then the reaction generally takes place with a substantially lower yield of the desired carboxylic acids.

In some cases reaction pressures as low as 20–50 atmospheres are adequate, but it has been found that pressures in excess of 100 atmospheres give optimum results. Pressures in the range of from about 200 to 500 atmospheres are useful although no advantage is evident for using pressures in excess of about 200 atmospheres.

When anhydrous conditions are used in the carbonylation reaction, the reaction product can be taken up in water, whereupon the carboxylic acid is formed and can be separated from any excess water which may be present by known means, i.e., extraction, distillation, decantation, and the like. The amount of water added to the reaction product can vary in such a way that from 0 to 20 parts by weight of water remain in the mixture of water, HF and isobutyric acid.

We have discovered that the hydrogen fluoride catalyst used in our process can conveniently and economically be separated from the carbonylation-hydrolysis product of the Koch reaction by means of an ion permeable membrane which preferentially permits removal of HF from the product. HF permeates the membrane to a much greater degree than isobutyric acid and in a staged separation apparatus the HF can be completely separated from the isobutyric acid product and the HF can then be recycled to the carbonylation reactor to again perform its function as a catalyst. The thus removed HF can be recycled for use again as catalyst in the carbonylation step.

The preferred cation permeable membrane can be a flat film or tubing of a polyfluoroethylene modified by sulfonic acid groups attached to carbon atoms.

The process of this invention has decided energy advantages of the prior art method involving vaporization or distillation of the components in the reaction product. Our process allows the separation of dissolved HF from the reaction product with no phase change and it does not require the energy of latent heat of vaporization.

Typical membranes useful in this invention are those known as Nafion ® and Teflon ® FeP which are marketed by DuPont. The Nafion ® products are described as being copolymers of tetrafluoroethylene and monomers such as perfluoro-3,6-dioxa-4-methyl-7-Octen sulfamic acid, having equivalent molecular weights in the range of 950–1800.

The process of this invention is meant to include all other designs known to be useful in the art of ion-permeable membrane use such as pressure filtration, centrifugation, staging, etc.

The process of this invention is further illustrated in the following example.

EXAMPLE

The reaction product from the carbonylation reaction of propylene, CO, HF and water containing 6.89 g. of HF, 7.29 g. of water, and 6.90 g. of isobutyric acid was added to a 30 ml. polypropylene vial (A) and the vial was then fitted and sealed with a Nafion 120 membrane disc at the mouth thereof. The disc has a diameter of 17.55 mm and an area of 240 mm². This vial was then inverted into a 16 oz. polypropylene jar (B) containing 355 g. of water and the apparatus was allowed to stand for 47 hours (at room temperature). At the end of this time the contents of each container were analyzed by gas chromatography for isobutyric acid content and for HF content by base titration and correction for the isobutyric acid present. The results are shown in the following table.

TABLE

|  | Initial Weight in Vial A | Final Weight After 47 Hours | |
|---|---|---|---|
|  |  | in Vial A | in Bottle B |
| Isobutyric Acid | 6.90 g. | 3.70 g. | 3.22 g. |
| HF | 6.89 g. | 2.92 g. | 3.73 g. |

It is apparent from this that HF permeates the membrane to a much greater degree (54.4%) than isobutyric acid (46.7%) and that in a staged separation apparatus the HF can be completely separated from the isobutyric acid product and the HF can then be recycled to the carbonylation reaction to again perform its function as catalyst.

We claim:

1. In the carbonylation of an olefin with carbon monoxide in the presence of hydrogen fluoride catalyst wherein the reaction product is treated with water to produce a mixture of a carboxylic acid, HF and optionally water, the improvement comprising contacting at a temperature in the range of from about 25° C. up to about 100° C., the mixture with one side of a cation permeable membrane of a copolymer of tetrafluoroethylene and perfluoro-3,6-dioxa-4-methyl-octen sulfamic acid whose other side is in contact with water.

2. The process of claim 1 wherein the weight ratio of water to other products in the mixture is from 0 to 20.

3. The process of claim 2 wherein the cation permeable fluoropolymer membrane is either in tubular or flat film form.

4. The process of claim 3 wherein the cation permeable fluoropolymer membrane is in the form of a flat film.